(12) United States Patent
Bouteiller

(10) Patent No.: US 9,051,292 B2
(45) Date of Patent: Jun. 9, 2015

(54) SULTONE COMPOUND DERIVATIVES SUBSTITUTED BY NUCLEOPHILES, IN PARTICULAR RADIONUCLIDES, AND USE THEREOF FOR MARKING MACROMOLECULES

(75) Inventor: Cedric Bouteiller, Vulbens (FR)

(73) Assignee: ADVANCED ACCELERATOR APPLICATIONS, Saint-Genis-Pouilly (FR)

( * ) Notice: Subject to any disclaimer, the term of this patent is extended or adjusted under 35 U.S.C. 154(b) by 74 days.

(21) Appl. No.: 13/389,837

(22) PCT Filed: Aug. 10, 2010

(86) PCT No.: PCT/EP2010/061646
§ 371 (c)(1),
(2), (4) Date: May 8, 2012

(87) PCT Pub. No.: WO2011/018467
PCT Pub. Date: Feb. 17, 2011

(65) Prior Publication Data
US 2012/0220785 A1    Aug. 30, 2012

(30) Foreign Application Priority Data
Aug. 11, 2009   (FR) ..................................... 09 55610

(51) Int. Cl.
| | | |
|---|---|---|
| C07D 327/04 | (2006.01) | |
| A61K 51/04 | (2006.01) | |
| A61K 51/08 | (2006.01) | |
| C07K 1/13 | (2006.01) | |

(52) U.S. Cl.
CPC .............. *C07D 327/04* (2013.01); *A61K 51/04* (2013.01); *A61K 51/08* (2013.01); *C07K 1/13* (2013.01); *A61K 51/082* (2013.01)

(58) Field of Classification Search
CPC .................................................. C07D 411/08
See application file for complete search history.

(56) References Cited

U.S. PATENT DOCUMENTS 4,064,167 A * 12/1977 DuBois et al. .................. 562/42
4,331,760 A    5/1982 Berger et al.

OTHER PUBLICATIONS

Brown, J.P., et al. "Flavonoid Sweetners. Synthesis and Intestinal Absorption of Selected Sulfoakylated Hesperetin-3-14C Derivatives in the Rat." Agricult. Food Chem. (1978), vol. 26, No. 6, pp. 1418-1422.*
Austin Hospital. "Radionuclides & Radiophamraceuticals." Available from: < http://www.petnm.unimelb.edu.au/pet/detail/radionuc.html >. Updated 2007.*
PerkinElmer Life Sciences. "Carbon-14 Handling Precautions." Available from: <http://shop.perkinelmer.com/content/pdfs/english/carbon14.pdf >. Updated 1999.*
Brown et al., "Flavonoid sweeteners. Synthesis and intestinal absorption of selected sulfoalkylated hesperetin-3-14C derivatives in the rat," J. Agricultural and Food Chem., 26(6):1418-22 (1978) XP002600959.
Bureeva et al., "Inhibition of classical pathway of complement activation with negative charged derivatives of bisphenol A and bisphenol disulphates," Bioorg. Med. Chem., 13(4):1046-1052 (2005) XP004776007.
Ikeda et al., "Methanesulfonic acid derivative of drugs. IV. Methanesulfonic acid derivative of p,p'-diaminodiphenylsulfone. I. Hydrolysis rate in vitro," Chem. Pharm. Bull., 21(6):1198-1204 (1973) XP002575503.
International Search Report and Written Opinion in PCT/EP2010/061646, dated Oct. 26, 2010.

* cited by examiner

*Primary Examiner* — Noble Jarrell
*Assistant Examiner* — John S Kenyon
(74) *Attorney, Agent, or Firm* — McAndrews Held & Malloy, Ltd.

(57) ABSTRACT

The invention relates to polysultone derivatives used as precursors to radiolabelled macromolecules usable for medicine and in nuclear imaging. The aim of the invention is to provide novel prosthetic compounds or groupings, the synthesis of which is straightforward, easy and automatable, enabling access to economical and effective radiolabelled macromolecules. The aim is achieved by the invention, which involves compounds of formula 10 or 11. Said double-sultone derivatives are produced by opening the sultone rings using a nucleophile radical $R^i$ which may be a radionucleide $R^*$ for one of the sultone rings and an active radical peptide $R^a$ for the other sultone ring. The invention also relates to the method for producing the abovementioned compounds, as well as to the drugs or diagnosis products that the latter are capable of forming.

7 Claims, No Drawings

SULTONE COMPOUND DERIVATIVES SUBSTITUTED BY NUCLEOPHILES, IN PARTICULAR RADIONUCLIDES, AND USE THEREOF FOR MARKING MACROMOLECULES

FIELD OF THE INVENTION

The field of the invention is that of complex bioactive chemical compounds with a high molecular weight (macromolecules), such as peptides, proteins and oligonucleotides, which can be used as precursors to (radio)pharmaceuticals.

The invention particularly relates to labelling strategies and methods for obtaining these macromolecules as well as use thereof, preferably once radiolabelled, in therapy (nuclear medicine i.a.) and/or in diagnosis (nuclear imaging i.a.) depending on the radioelement.

PRIOR ART

Macromolecules are increasingly being proposed as (radio)pharmaceutical compounds and their applications seem to be very promising particularly in nuclear medicine and oncology. A recent article[1] on labelling macromolecules with fluorine-18 cites a study which predicts that peptides alone will represent approximately 50% of drugs at the clinical stage in the next few years. These peptides are also potential radioactive tracers for medical imaging, in particular for Positron Emission Tomography (PET) or Emission Tomography.

In the particular case of PET, there are at present few examples of macromolecules labelled with fluorine-18. Radioactive labellings of proteins have up till now been carried out mainly with radioactive metals by complexing ($^{99m}$Tc, $^{68}$Ga, $^{111}$In). The advantages of fluorine-18 as a PET radioisotope linked to the development of cyclotron installations in France and worldwide, mean that the development of methods for fluorine-18 labelling of these macromolecules is now undeniably arousing interest.

Radiofluorination reactions with fluorine-18 depend on the labelled precursor obtained during the production of the radioactive atom. The fluorine-18 can be obtained in its electrophilic form [$^{18}$F]—F$_2$ (used in electrophilic reactions in this form or in the form of less reactive hypofluorite[2,3] [$^{18}$F]—AcOF) or in its nucleophilic form [18F]—F$^-$ (used in nucleophilic reactions).

The electrophilic fluorination reaction is difficult to implement and subject to numerous limitations. By this radiosynthesis route, the radiochemical yield of fluorinated products is limited to 50% (starting from [$^{18}$F]—F$_2$, only one of the two fluorine atoms is labelled and is incorporated in the reagent or the product) and the final specific radioactivity is less than 20 mCi/μmol (0.74 GBq/μmol). This method of radiosynthesis is therefore not suited to tracers intended for receptor quantification and distribution studies. It is the method which was initially used for preparing [$^{18}$F]-FDG and which is still used for preparing [$^{18}$F]-Fluoro-L-DOPA[4].

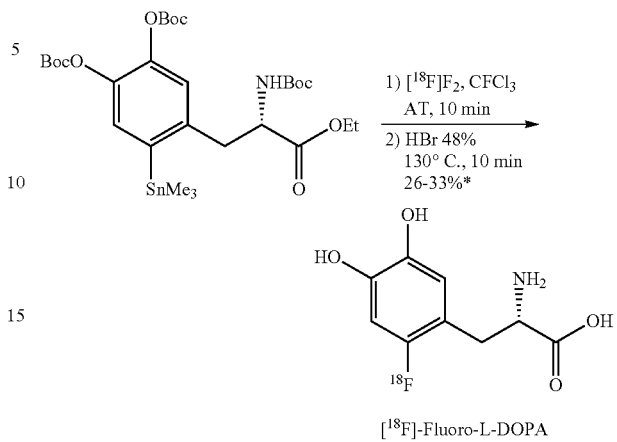

Figure 1: radiosynthesis of [$^{18}$F]-L-DOPA

*Radiochemical yield calculated starting from [$^{18}$F]F$_2$ and corrected by the decrease Ogawa et al.[5] have described fluorine-18 labelling of the cyclic pentapeptide cyclo(RGDfMeV) below by direct electrophilic reaction of the phenyl ring of the tyrosine unit with hypofluorite [$^{18}$F]F]-AcOF.

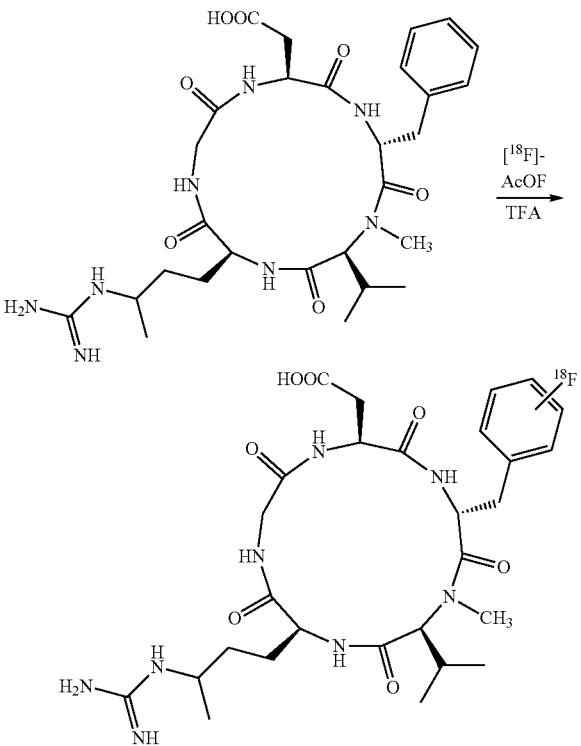

Figure 2: Fluorine-18 labelling of cyclic cyclo(RGDfMeV)

However, in addition to the abovementioned limits of the electrophilic route (low radiochemical yield, low specific radioactivity), this synthesis has the drawback of leading to a multitude of compounds (regioisomers, mono- or di-fluorinated compounds) which cannot be separated. Moreover, as methionine, cysteine and tryptophan can be oxidized by hypofluorite, this method is not applicable to the labelling of peptides containing these amino acids which are sensitive to oxidation. The [$^{18}$F]—F$^-$ ion produced by the cyclotron is recovered in aqueous solution. As it is, it offers very few synthesis possibilities.[6] Due to its high energy of solvation (>100 kJ·mol$^{-1}$), it is only very slightly nucleophilic in the presence of water. In order to increase its nucleophilic character, it is converted to anhydrous salt with a large cation (cesium, rubidium, tetraalkylammonium) or brought into contact with cryptand when the counter-ion is potassium[7] and dried. The nucleophilic substitution reaction is carried out in strongly dissociating solvents (aprotic polar) such as DiMethylFormaldehyde (DMF), DiMethylSulphOxide (DMSO) or acetonitrile. Most of the radiopharmaceutical compounds labelled with fluorine-18 have been synthesized by nucleophilic substitution mainly in aliphatic series and homoaromatic series. The best-known example is the radiosynthesis of [$^{18}$F]-FDG[8].

Figure 3: Radiosynthesis of [$^{18}$F]-FDG

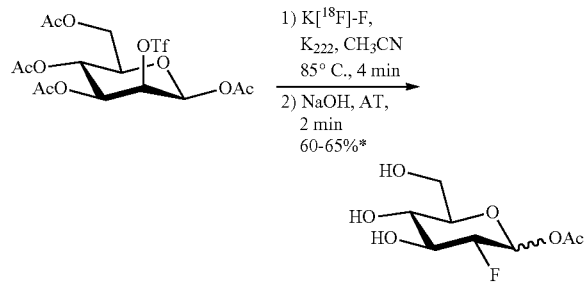

*Radiochemical yield calculated starting from K[$^{18}$F] and corrected by the decrease The peptides and proteins comprise numerous labile protons (hydroxyls, amides, amines, thiols, acids) for which protection cannot always be envisaged, which means that most often the direct labelling of these macromolecules by nucleophilic substitution cannot be envisaged.

The introduction of a fluorine-18 into a macromolecule of peptidic nature is most often carried out via a prosthetic group bearing the radioisotope[1]. This approach then involves the preparation of the functionalized and radiolabelled prosthetic group followed by its conjugation with a reactive function of the peptide or protein. This strategy has the advantage of making it possible to use severe conditions for the preparation of the radiolabelled prosthetic entity, the conjugation of the latter to the macromolecule then being able to be carried out under mild conditions in order to preserve its integrity.

A certain number of prosthetic groups labelled with fluorine-18 are described in the literature. They can be classified according to their reactive function and the type of reaction by which they are coupled to the macromolecule (amines, hydrazines, oximes, acids, aldehydes etc.). Most of them are designed to be coupled directly to a peptide or a protein via an amine function of an amino acid residue (N-terminal α-NH$_2$ or internal ε-NH2 of a lysine) or optionally via an alkylamino spacer. They are characterized by a carboxylic acid ([$^{18}$F]-AFB) or activated ester function (ester of N-hydrosuccinimide [$^{184}$F]-SFB or nitrophenyl).

All these radiolabelled prosthetic groups are differentiated by their accessibility as regards radiosynthesis (nature and ease of synthesis of the radiolabelling precursor, effectiveness of the fluorination stage, total number of radiosynthesis stages, overall radiochemical yield, purification), their effectiveness in the conjugation reaction and their in vivo stability.

In addition to the constraints relating to the chemistry of fluorine-18, the manufacturers of these radiolabelled compounds are faced with constraints relating to the automation of the synthesis of these compounds in its entirety. In fact, the pharmaceutical standards (GMP), just as much as radiological protection make it impossible to carry out these syntheses without automated equipment. All of this militates in favour of limiting the number of stages and the purification facilities in this type of synthesis.

OBJECTIVES AND TECHNICAL PROBLEM

Taking account of this prior art, the present invention aims to remedy the drawbacks of the prior art and to satisfy at least one of the following essential objectives:

To provide novel prosthetic groups the synthesis of which is straightforward, easy, and automatable, and which are capable of constituting precursors for labelling macromolecules for the development of economical and effective (radio)pharmaceuticals.

To provide novel prosthetic groups the synthesis of which is straightforward, easy, and automatable, and which are capable of constituting universal precursors for labelling macromolecules for the development of (radio)pharmaceuticals by the same synthesis route.

To provide novel prosthetic groups the synthesis of which is straightforward, easy, and automatable, and which are capable of constituting novel precursors for labelling macromolecules for the development of (radio)pharmaceuticals irrespective of the radionuclide concerned, e.g. iodine, chlorine or also fluorine.

To provide a novel method for labelling macromolecules via coupling with a prosthetic group of a novel family for the development of (radio)pharmaceuticals, which is straightforward, easy, and automatable, said method offering at least one of the following advantages:
  a reduction in synthesis stages (for example 2 vs. 3-5 for the other labelling methods via other groups, in particular prosthetic),
  an increase in (radio)chemical yields at very low temperatures and within very short periods of time,
  ease of separation of the intermediate and final compounds,
  no production of by-products,
  suitability for labelling numerous macromolecules,
  possibility of carrying out the coupling of the radionuclide(s) with the macromolecule in water.

To provide novel drugs and/or effective and economical radioactive tracers, from this novel macromolecule labelling method.

To provide a novel use of sultone derivatives for labelling macromolecules with a nucleophilic radionuclide.

To provide a novel use of sultones as binding entities between two nucleophiles or structures bearing a nucleophile, by opening the sultone rings.

BRIEF DESCRIPTION OF THE INVENTION

These objectives, among others, are satisfied by the invention which, in a first aspect relates to new compounds derived from disultone-type precursors, preferably polysultones. These new compounds are characterized in that they are each obtained by substitution of a precursor which comprises at least two sultones linked to each other by at least one spacer and of which the formula (1) is as follows:

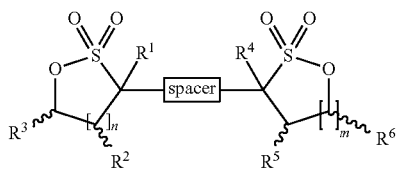

in which
- the $R^1$ to $R^6$ groups, identical or different, correspond to hydrogen or an alkyl, aryl, arylalkyl, alkylaryl, acyl, cycloalkyl; $R^3$ to $R^6$ corresponding preferably to hydrogen;
- n, m is an integer, preferably comprised between 0 and 2;
- the spacer is a divalent structure, preferably selected from those comprising one or more aromatic, alkyl, alkene or alkyne groups optionally combined together; by opening at least one of the sultone rings using at least one nucleophilic radical and preferably at least one (preferably one) nucleophilic radical $R^i$ on each of the opened sultone rings.

Preferably, the compounds according to the invention are compounds of general formula 2 or 3

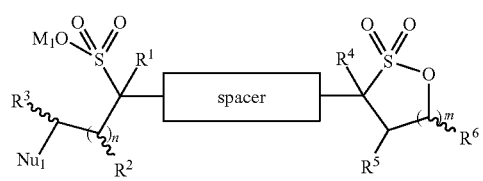

$Nu_1$ = Nucleophile 1
$M_1$ = Counter-ion 1 ($K^+$, $Na^+$, ...)

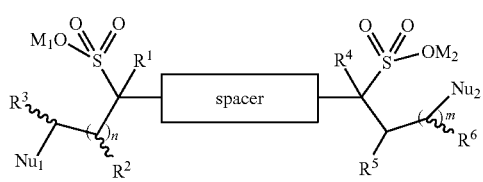

$Nu_1$ = Nucleophile 1
$M_1$ = Counter-ion 1 ($K^+$, $Na^+$, ...)
$Nu_2$ = Nucleophile 2
$M_2$ = Counter-ion 2 ($K^+$, $Na^+$, ...)

formulae in which:
- $Nu_1$, $Nu_2$ are nucleophiles identical to or different from each other;
- $M_1$, $M_2$ are counter-anions identical to or different from each other and chosen from the cations, preferably from the group of the monovalent cations, for example $K^+$, $Na^+$.

In a second aspect, a subject of the invention is new precursors 1 each comprising at least two sultones linked to each other by at least one spacer characterized in that they correspond to one of the following formulae:

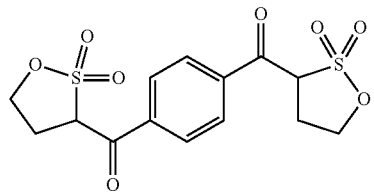

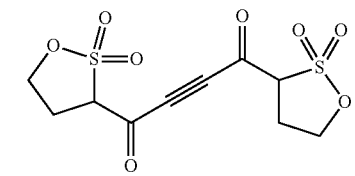

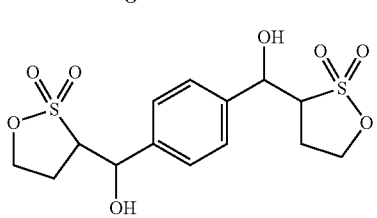

A particular sub-group of the precursors 1 comprises:

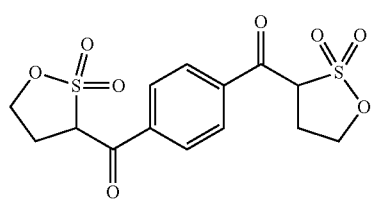

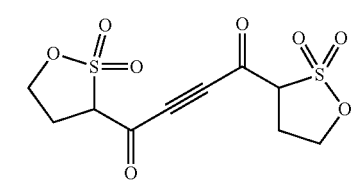

In a third aspect, a subject of the invention is a method for the synthesis of precursors 1 each comprising at least two sultones linked to each other by at least one spacer, characterized in that it essentially consists of reacting sultones—advantageously butane sultones, propane sultones and/or ethane sultones—and a polyester, preferably by a mechanism of lithiation of each alpha-sulphur of the sultone followed by a reaction with the electrophilic polyester which is added to the reaction medium for this purpose.

In a fourth aspect, a subject of the invention is a method for the synthesis of the compounds derived from polysultone precursors 1 characterized in that it comprises the following stages:
a. Utilization or synthesis of a polysultone, preferably a double sultone, each comprising at least two sultones linked to each other by at least one spacer;
b. Opening of one of the sultones with a first nucleophile leading to the formation of a sulphonate;
c. Separation of the polysultone (preferably the double sultone) precursor of the formed sulphonate by the difference in polarity;

d. Collection of the formed sulphonate;
e. Coupling of the formed sulphonate with at least one second (preferably one) nucleophile by the opening of a (preferably the) second sultone;
f. Collection of the polysulphonate (preferably disulphonate) obtained in stage e.

In a fifth aspect, the invention relates to a drug or a diagnosis product (tracer) comprising at least one compound according to the invention or obtained by one of the methods according to the invention.

In a sixth aspect, the invention relates to the use of the compounds according to the invention or obtained by the method according to the invention for labelling macromolecules with nucleophilic radionuclides,
or as binding entities between two nucleophiles or structures bearing a nucleophile, by opening the sultone rings.

The main advantages of the invention are the following:
Use of the same approach for labelling irrespective of the radionuclide;
Reduction in the number of synthesis stages;
Obtaining very high radiochemical yields at very low temperatures and within very short periods of time;
Possibility of separating the starting precursor (very apolar) form the product formed (very polar);
No production of by-products;
Possibility of automation;
Suitability for labelling numerous macromolecules;
Coupling with the possible macromolecule in water;
Simplicity;
Economy;
Access to novel compounds opening up multiple therapeutic and diagnostic developments.

DETAILED DESCRIPTION OF THE INVENTION

In the general formulae of the novel compounds 1, 2, 3, reference is made to the following definitions:

"alkyl" corresponds for example to a linear, branched or cyclic saturated monovalent C1-C30 alkyl group, preferably C1-C20, and, even more preferentially C1-C10, optionally substituted, comprising or not comprising heteroatoms. Examples of alkyl groups are in particular methyl, ethyl, isopropyl, n-propyl, tert-butyl, isobutyl, n-butyl, n-pentyl, isoamyl and 1,1-dimethylpropyl.

"aryl" corresponds for example to one or more monocyclic or polycyclic and preferably monocyclic or bicyclic condensed or uncondensed aromatic monovalent groups, having 6 to 18 carbon atoms. It must be understood that, within the framework of the invention, by polycyclic aromatic radical is meant a radical having two or more aromatic rings, condensed (orthocondensed or ortho- and pericondensed) with each other, i.e. having, in pairs, at least two carbon atoms in common. Said aromatic hydrocarbon group ("aryl") is optionally substituted for example by one or more $C_1$-$C_3$ alkyls, one or more halogenated hydrocarbon radicals (e.g. $CF_3$), one or more alkoxy (e.g. $CH_3O$) or one or more hydrocarbon radicals comprising one or more ketone units (e.g. $CH_3CO—$). By way of examples of aryls, there can be mentioned the phenyl, naphthyl, anthryl and phenanthryl radicals.

"arylalkyl" corresponds for example to an alkyl group as defined above, substituted by one or more aryl groups on its hydrocarbon chain, the aryl group being as defined above. Examples of this are benzyl and triphenylmethyl.

"alkylaryl" corresponds for example to monovalent alkyl, substituted or linked to one or more monovalent aromatic groups, optionally substituted.

By "acyl" is meant an $R_0$—CO— group where $R_0$ represents alkyl as defined above; or an Ar—CO— group where Ar represents an aryl group as defined above, or arylalkyl in which aryl and alkyl are as defined above and in which the aryl part is optionally substituted e.g. by alkyl.

By "cycloalkyl" is meant a mono- or polycyclic, preferably mono- or bicyclic, saturated hydrocarbon radical preferably having from 3 to 10 carbon atoms, even better from 3 to 8. By polycyclic saturated hydrocarbon radical is meant a radical having two or more cyclic rings attached to each other by σ bonds and/or condensed in pairs. Examples of polycyclic cycloalkyl groups are adamantane and norbornane. Examples of monocyclic cycloalkyl groups are cyclopropyl, cyclobutyl, cyclopentyl, cyclohexyl, cycloheptyl and cyclooctyl.

By "alkene" or "alkenyl" is meant e.g. a substituted or unsubstituted, linear or branched, unsaturated hydrocarbon chain, having at least one olefinic double bond, and more preferably a single double bond. Preferably, the alkenyl group has 2 to 8 carbon atoms, even better 2 to 6. This hydrocarbon chain optionally comprises at least one heteroatom such as O, N, S. Preferred examples of alkenyl groups are the allyl and homoallyl groups.

By "alkyne" or "alkynyl" is meant e.g. according to the invention, a substituted or unsubstituted, linear or branched, unsaturated hydrocarbon chain, having at least one acetylenic triple bond, and more preferably a single triple bond. Preferably, the alkynyl group has 2 to 8 carbon atoms, even better 2 to 6 carbon atoms. By way of example, there can be mentioned the acetylenyl group, as well as the propargyl group. This hydrocarbon chain optionally comprises at least one heteroatom such as O, N, S.

The spacer can for example be an aromatic structure (functionalized or not), an alkyne structure or any other structure. In the simplest cases, the $R^1$-$R^6$ groups are protons (in particular in the $R^6$ and $R^3$ nucleophilic attack positions) but they can also be any other group.

The precursors 1 according to the invention can be disultones with the following formulae:

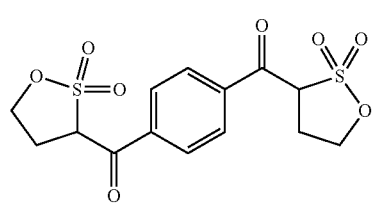

1a

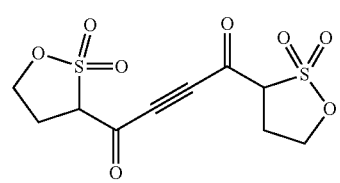

1b

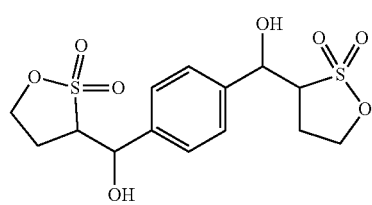

1c

-continued

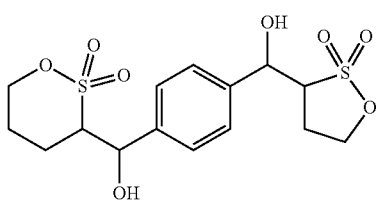

1d

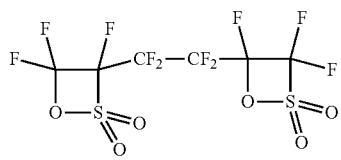

1e

Figure 4: Structure of the sultones

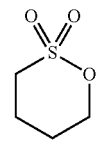

Butane sultone

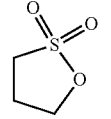

Propane sultone

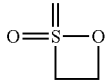

Ethane sultone

The structure 1a corresponds to the case where the spacer is an aromatic ring linked to the two sultones by two ketone functions in the para position, where the $R^1$-$R^6$ groups are all hydrogens and where n=m=1.

The structure 1b corresponds to the case where the spacer is an alkyne linked to the two sultones by two ketone functions, where the $R^1$-$R^6$ groups are all hydrogens and where n=m=1.

The structure 1c corresponds to the case where the spacer is an aromatic ring linked to the two sultones by two alcohol functions, where the $R^1$-$R^6$ groups are all hydrogens and where n=m=1.

The structure 1d corresponds to the case where the spacer is an aromatic ring linked to the two sultones by two alcohol functions in the para position, where the $R^1$-$R^6$ groups are all hydrogens and where n=2 and m=1.

The structure 1e corresponds to the case where the spacer is a tetrafluoroethane unit directly linking the two sultones, where the $R^1$-$R^6$ groups are all fluorines and where n=m=0.

Synthesis of the Polysultones

These compounds can be synthesized from commercial products.

Thus, the method for synthesizing the compound according to the invention essentially consists of reacting sultones—advantageously butane sultones, propane sultones and/or ethane sultones—and for example a polyester, preferably according to a mechanism of lithiation of each alpha-sulphur of the sultone followed by a reaction with the electrophilic polyester which is added to the reaction medium for this purpose.

For example, two equivalents of the corresponding sultone and one equivalent of a diester corresponding to the spacer via a reaction of lithiation of the alpha-sulphur of the sultone followed by the reaction with the diester as electrophile.

This synthesis is based on the chemistry of the sultones, cyclic compounds which are sulphur-containing lactone analogues with 4, 5 or 6 members (Figure 4).

The sultones are well known for their reactivity with nucleophiles[11,12]. This type of reactivity was moreover already the subject of a patent filed in 2004[13]. The reaction forms a carbon-nucleophile bond by nucleophilic attack on the alpha-carbon of the oxygen and results in the formation of a sulphonate function. The reactivity of the sultones with the nucleophiles such as the cyanides phosphines[14,15], amines[16,17,18], alcoholates[16,19] thiolates[20], iodine, chlorine and bromine[19,21,22] is well known.

The synthesis diagram of the compound 1a is represented below in Figure 5. The lithiation of the alpha-sulphur of two equivalents of propane sultone at −78° C. in THF over 30 minutes followed by the addition of 1 equivalent of the methyl (or paranitrophenyl) diester leads to the corresponding disultone 1a. The examples which follow illustrate this synthesis.

Figure 5: Example of the synthesis of the double sultone 1a

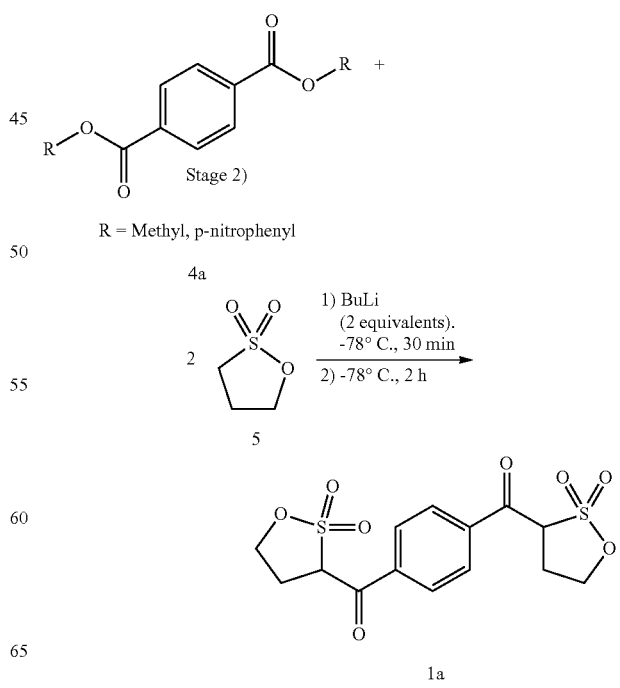

The synthesis diagram of the compound 1b is represented below in Figure 6. The lithiation of the alpha-sulphur of two equivalents of propane sultone at −78° C. in THF over 30 minutes followed by the addition of 1 equivalent of commercial butynedioic acid methyl diester. The examples which follow illustrate this synthesis.

Figure 6: Example of the synthesis of the double sultone 1b

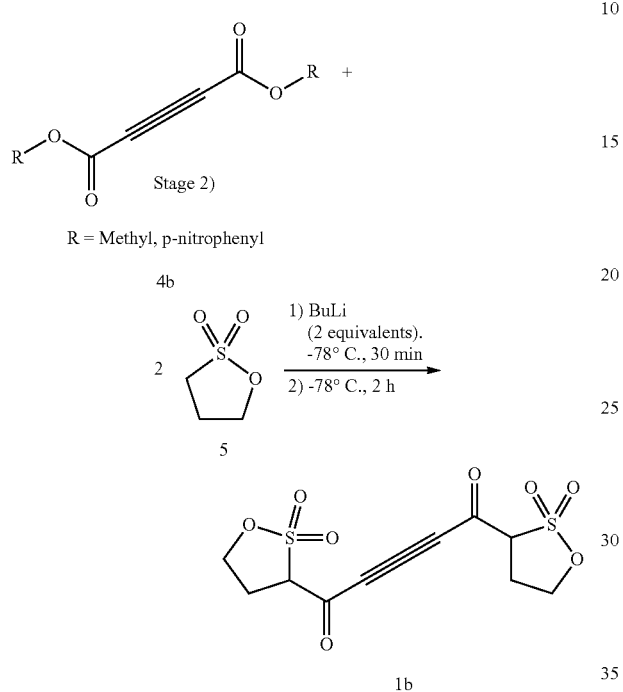

These polysultones, and, in particular, the double sultones 1a and 1b) can for example be used:
either as a "linker", a binding entity, between two nucleophiles or structures bearing a nucleophile by opening of the sultone rings,
or according to a preferred but non-limitative embodiment of the invention:
for labelling macromolecules (bearing the nucleophile opening the second sultone) with a nucleophilic radionuclide (opening the first sultone) such as for example fluorine-18, bromine-76, iodine-123, iodine-131 or any other nucleophilic radionuclide as well as all combinations of nucleophilic radionuclides.

The polysultone precursors 1 defined above give access to novel compounds each substituted by at least one nucleophilic radical by opening at least one of the sultone rings, preferably by at least one (preferably one) nucleophilic radical $R^i$ on each of the opened sultone rings. Advantageously, the nucleophilic radical(s) $R^i$ is (are) one or more radionuclide(s) $R^*$, preferably selected from the group comprising fluorine-18, bromine-76, iodine-123, iodine-131 or any other nucleophilic radionuclide.

Preferably, the nucleophilic radical(s) $R^i$ is (are) one or more active radical(s) $R^a$ selected from the group comprising the peptides, the proteins, the oligonucleotides, the polynucleotides or any other macromolecule.

Even more preferentially, by way of example starting from 1a and 1b these compounds correspond to the following formulae 6a or 6b:

The more particularly preferred compounds according to the invention are compounds having at least one substitution by a radioactive group and at least one substitution by an active group of macromolecule type (for example in therapy or in diagnosis). Each of these compounds is characterized in that it is substituted by one or more radionuclide(s), preferably selected from the group comprising fluorine-18, bromine-76, iodine-123, iodine-131 or any other nucleophilic radionuclide, by opening one of the sultone rings and in that it is substituted by a nucleophilic radical selected from the group comprising the peptides, proteins, oligonucleotides, polynucleotides or any other macromolecule by opening the other sultone ring optionally via the attack of a free amine.

More precisely, by way of example starting from 1a and 1b these preferred compounds correspond e.g. to the following formulae 7a or 7b respectively:

Obtaining the Compounds According to the Invention

According to the invention, the method for obtaining a novel compound originating from a poly-(e.g. double) sultone precursor is characterized in that it comprises the following stages:

a. Utilization or synthesis of a polysultone, preferably a double sultone, of formulae 1a, 1b, or 1c;
b. Opening of one of the sultones with a first nucleophile leading to the formation of a sulphonate;
c. Separation of the polysultone (preferably the double sultone) precursor and of the formed sulphonate by difference in polarity;
d. Collection of the formed sulphonate;
e. Coupling of the formed sulphonate with at least one second nucleophile by opening a (preferably the) second sultone;
f. Collection of the polysulphonate (preferably disulphonate) obtained in stage e.

By way of example, the labelling of macromolecules with fluorine-18 is represented in Figure 7 below. The product 1a is radiofluorinated under standard radiofluorination conditions and the resultant (very polar) fluorosulphonate 8 is easily separated from the (apolar) disultone precursor 1a via a C18 cartridge due to their differences in polarity. The experimental part of the synthesis of the non-radioactive reference [$^{19}$F]-8 and of the radiosynthesis of the product [$^{18}$F]-8 is described in the examples which follow.

The obtained fluorosulphonate 8 is then coupled in water (solubility of the fluorosulphonate in aqueous medium) with a peptide by opening the second sultone with a free amine borne by the peptide leading to the radiofluorinated peptide 9.

Figure 7: Fluorination of the sultone 1a, purification and coupling with a peptide

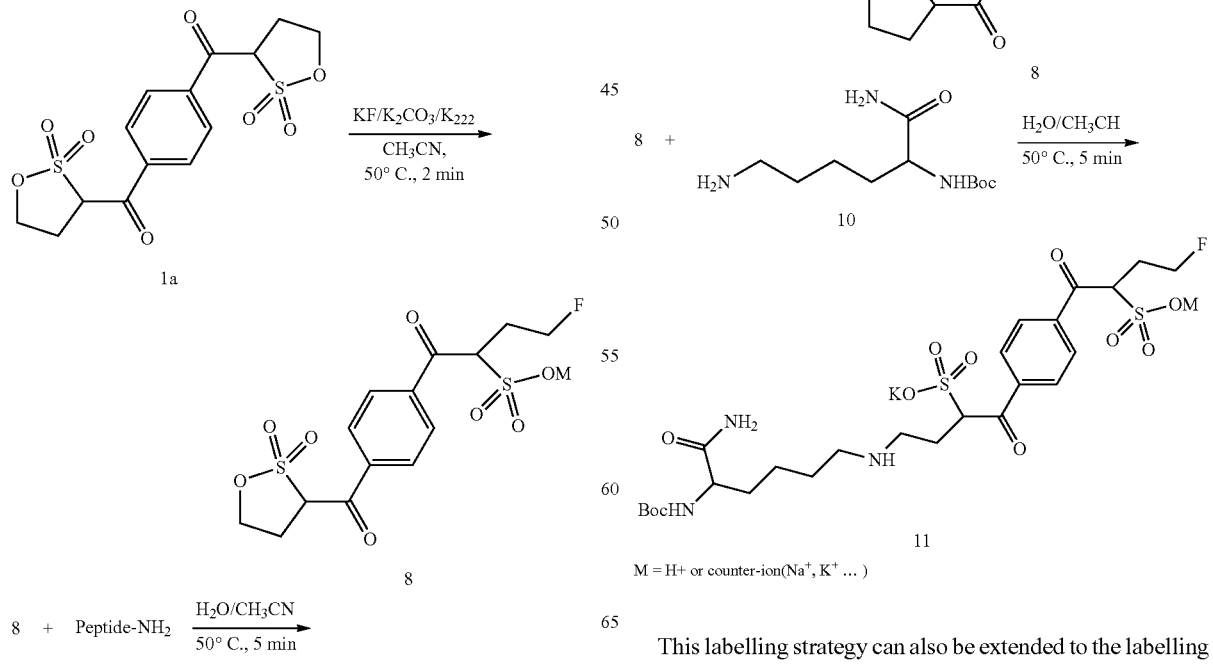

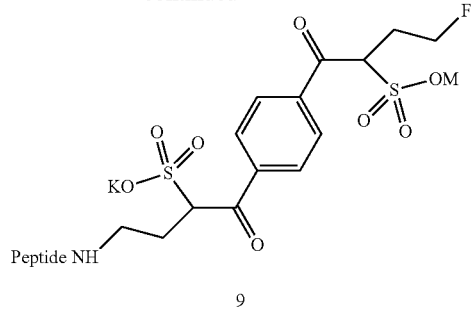

M = H+ or counter-ion (Na$^+$,K$^+$...)

By way of example, the use of the Boc-Lysine-NH$_2$ 10 makes it possible to obtain the radiofluorinated Boc lysine 11: Figure 7. The procedure for the synthesis of [$^{19}$F]-11 and the radiosynthesis of [$^{18}$F]-11 are described in the examples which follow.

Figure 8: Fluorine-18 labelling of the Boc-Lysine-NH$_2$ 10 via the double sultones method

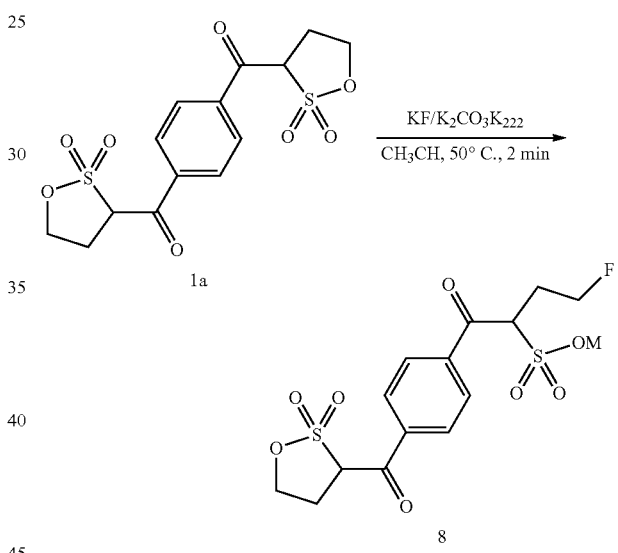

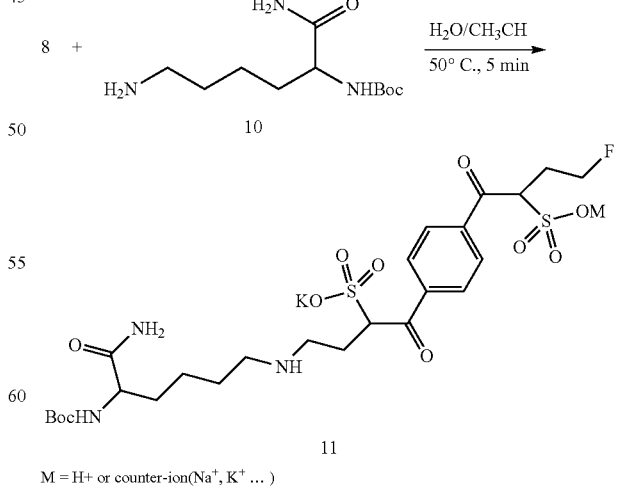

M = H+ or counter-ion(Na$^+$, K$^+$ ... )

This labelling strategy can also be extended to the labelling of the Boc-Lysine-NH$_2$ 10 with iodine. The iodized analogue 12 is obtained by coupling the Boc-lysine 10 with the iodized sultone 13, itself obtained by radioiodination of the disultone 1a. (see Figure 9 below). A description of the procedure for the synthesis of 13 by non-radioactive chemistry is appended in the examples which follow.

Figure 9: Labelling of the Boc-Lysine-NH2 with iodine

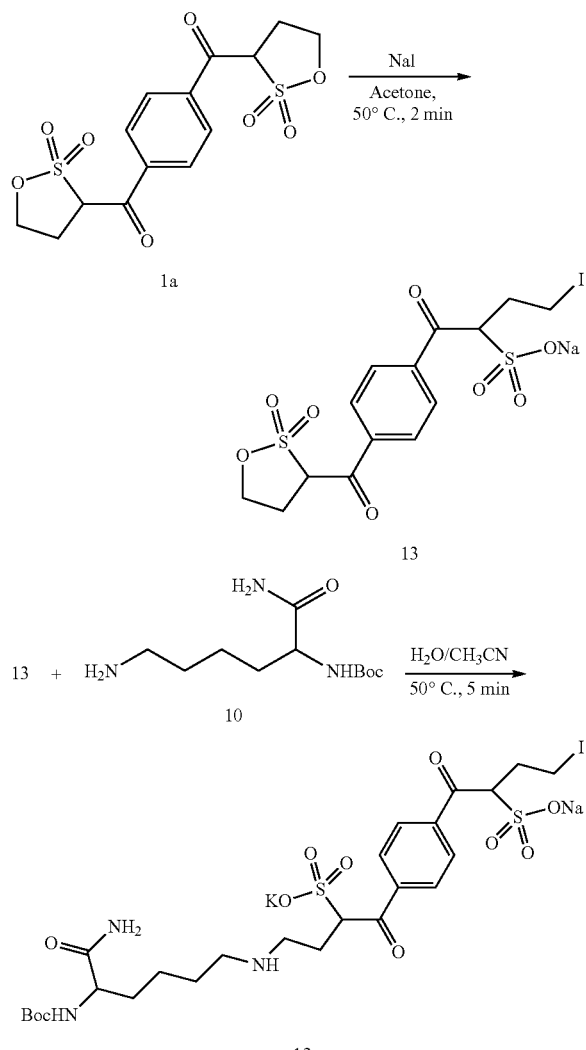

In the same way, the use of the RGD amino peptide 14 as a labelling precursor makes it possible to obtain the radiofluorinated peptide 15: Figure 10.

Figure 10: Fluorine-18 labelling of the RGD peptide via the double-sultone method

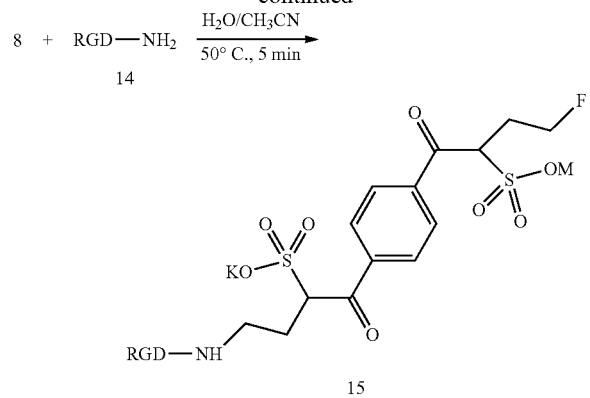

This labelling strategy can also be extended to the labelling of the RGD peptide 14 with iodine. The iodized analogue 16 is obtained by coupling the peptide precursor 14 with the iodized sultone 13, itself obtained by radioiodination of the disultone 1a. A description of the procedure for the synthesis of 13 by non-radioactive chemistry is appended in the experimental part.

Figure 10: Iodine-123 labeling of the RGD peptide

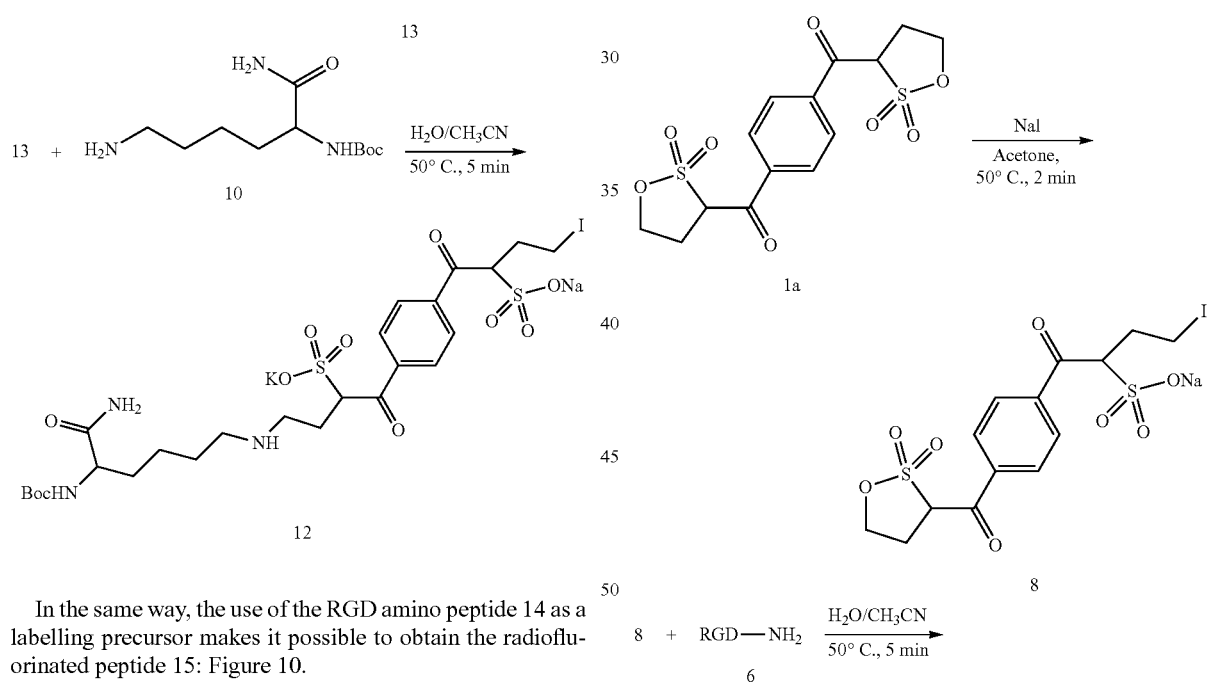

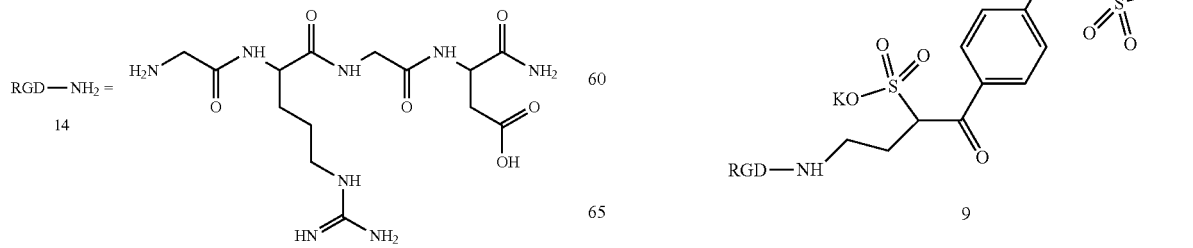

This labelling strategy will therefore make it possible to have the same single method for labelling, for example, a peptide with iodine-123 (for use in SPECT) or with fluorine-18 (for use in PET).

EXAMPLES

HPLC Methods

System A: analytical HPLC (Hypersil gold $C_{18}$ column, 5 µm, 4.6×100 mm) with $CH_3CN$ and 0.1% trifluoroacetic acid in water as eluents (0.1%, v/v, pH 2.0) [100% TFA (5 min), then linear gradient from 0% to 80% (40 min) with $CH_3CN$] at a flow rate of 1 mL/min. The UV detections are carried out at 265 and 254 nm.

System B: semi-preparative HPLC (Hypersil gold $C_{18}$ column, 5 µm, 21.2×250 mm) with $CH_3CN$ and 0.1% trifluoroacetic acid in water as eluents (0.1%, v/v, pH 2.0) [100% TFA (10 min), then linear gradient from 0% to 5% with $CH_3CN$ (2 min), then linear gradient from 5% to 70% in $CH_3CN$ (65 min)] at a flow rate of 1 mL/min. The UV detections are carried out at 265 and 254 nm.

System C: analytical HPLC (Hypersil gold $C_{18}$ column, 5 µm, 4.6×100 mm) with $CH_3CN$ and 25 mM of triethylammonium acetate in water as eluents (TEAA, 25 mM, pH 7.0) [100% TEAA (10 min), then linear gradient from 0% to 80% (40 min) with $CH_3CN$] at a flow rate of 1 mL/min. The UV detections are carried out in the max-plot mode (each peak is detected at its absorption maximum).

System D: semi-preparative HPLC (Hypersil gold $C_{18}$ column, 5 µm, 10×250 mm) with $CH_3CN$ and 50 mM of aqueous trimethylammonium bicarbonate as eluents (TEAB, 50 mM, pH 7.5) [100% TEAB (10 min), then linear gradient from 0% to 5% (2 min) with $CH_3CN$, then linear gradient from 5% to 18% with $CH_3CN$ (13 min), then linear gradient from 18% to 25% (14 min) with $CH_3CN$, then linear gradient from 25% to 31% (6 min) with $CH_3CN$, then linear gradient from 31% to 61% (15 min) with $CH_3CN$] at a flow rate of 1 mL/min. The UV detection is carried out at 254 and 220 nm.

Example 1

Synthesis of the Sultone 1a

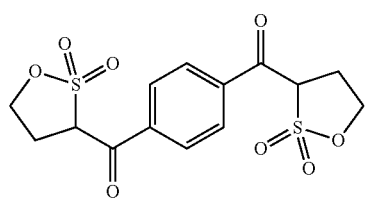

A 1.3 M solution of nBuLi in hexane (2.82 mL, 3.67 mmol, 1.99 eq) is added dropwise to a solution of 1,3-propane sultone (447 mg, 3.66 mmol, 2 eq) in THF (5 mL), under an argon atmosphere, at −78° C. After 1 h at −78° C., a solution of dimethyl terephthalate (358 mg, 1.84 mmol, 1 eq) in 10 mL of THF is added dropwise to the vigorously stirred previous mixture. The mixture is then stirred at −78° C. for 2 h 30 then, still at −78° C., the reaction is quenched with 1 mL of glacial acetic acid in 3 mL of THF (pH~6).

The mixture is then slowly warmed to AT then diluted in 20 mL of saturated NaCl in water and 50 mL of ethyl acetate. A solid is observed between the organic phase and the aqueous phase and is filtered off. The aqueous phase is washed with 30 mL of ethyl acetate. The organic phases are combined, dried with $MgSO_4$, filtered and concentrated under vacuum.

The crude product obtained is then purified by flash chromatography on a silica column with an acetone-cyclohexane mixture (2:3, v/v) as mobile phase. The bis-sultone, obtained is isolated in the form of a beige solid (270 mg, yield 40%). $R_f$ 0.42 (acetone-cyclohexane, 2:3, v/v);

$^1$H NMR (300 MHz, acetone-$d_6$,): δ 8.20 (s, 4H), 5.63-5.57 (m, 2H), 4.59-4.49 (m, 4H), 3.17-3.08 (m, 2H), 2.80-2.71 (m, 2H).

$^{13}$C NMR (75 MHz, DMSO-d6): δ 195.4, 140.8, 128.4, 63.3, 58.8, 32.2

HPLC (system A): $t_R$=26.7 min (purity 96.6%);

UV (recorded during the HPLC analysis): $λ_{max}$ 265 nm;

MS (ESI, negative mode): m/z 373.27 [M+H]$^-$ $C_{14}H_{14}O_8S_2$ 374.01

Example 2

Synthesis of the Monofluorinated Bis-Sultone 8:

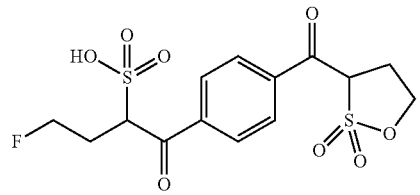 [SMILES: O=C(c1ccc(C(=O)C2CCOS2(=O)=O)cc1)C(CCF)S(=O)(=O)O]

200 µL of a solution of potassium fluoride in mQ water (62.2 mg/mL, 12.44 mg, 0.214 mmol, 1 eq), kryptofix (95 mg, 0.252 mmol, 1.18 eq) and 1 mL of acetonitrile are introduced into a flask. The bis-sultone 1a (80 mg, 0.214 mmol, 1 eq) in solution in 5.5 mL of acetonitrile is then added. The mixture is stirred at AT and progress is monitored using HPLC (System A).

The crude product of the reaction is purified by semi-preparative HPLC. After identification by mass spectrometry, the fraction containing the product is lyophilized. The product is obtained in the form of a beige solid (27.4 mg, 32.5%).

$^1$H NMR (300 MHz, MeOD-$d_3$,): δ 8.16-8.09 (m, 4H), 5.56-5.50 (ddd, J=2.46, 6.6, 8.67 Hz, 1H), 5.07-5.02 (ddd, J=0.96, 3.96, 9.42 Hz, 1H), 4.61-4.46 (m, 2H), 4.45-4.37 (m, 1H), 4.29-4.21 (m, 1H), 3.15-3.04 (m, 1H), 2.71-2.58 (m, 1H), 2.55-2.33 (m, 2H).

HPLC (system A): $t_R$=18.8 (dia1)–19 (dia2) min (purity 85%);

UV (recorded during the HPLC analysis): $λ_{max}$ 265 nm;

MS (ESI, negative mode): m/z 393.13 [M−H]$^-$ $C_{14}FH_{15}O_8S_2$ 394.02

Example 3

Synthesis of the Fluorinated Boc-Lysine 11:

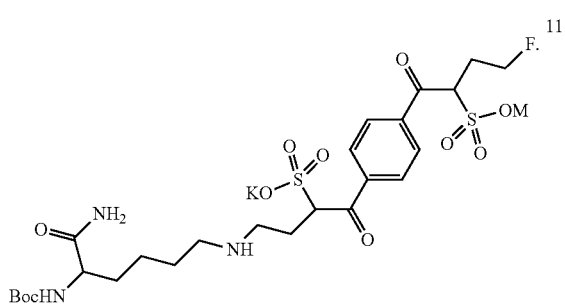

Boc-Lys-NH$_2$ (21.5 mg, 0.088 mmol, 1.1 eq) in DMF (0.8 mL) is added to a solution of the fluorinated sultone 8 (31.5 mg, 0.08 mmol, 1 eq) in DMF (1.8 mL), at ambient temperature. The reaction is monitored by HPLC (System A). Once the double sultone has been completely consumed, the crude product is purified by semi-preparative HPLC (System B). The mass analyses carried out have made it possible to isolate the correct fractions. A treatment on a Dowex resin (Dowex® 50WX8-400) is then necessary in order to reprotonate the sulphonate functions. A last purification on a semi-preparative column is then necessary in order to separate the cleavage product from the boc group due to the acid treatment via the resin. The final product is obtained in the form of a white solid (2.8 mg, 7.3%).

$^1$H NMR (DMSO, 300 MHz) δ 8.20-8.17 (dd, 2H), 7.82-7.77 (t, J=Hz, 2H), 4.93-4.91 (m, 1H), 4.51-4.42 (m, 1H), 4.24 (t, J=8.6 Hz, 2H), 3.77 (t, J=7.4 Hz, 2H), 2.67-2.60 (m, 2H), 1.77-1.74 (m, 2H), 1.65-1.55 (m, 2H), 1.37 (s, 9H), 1.31-1.24 (m, 2H).

HPLC (system C): $t_R$=15.8 (dia1)–16 (dia2) min (purity 97.3%);

UV (recorded during the HPLC analysis): $\lambda_{max}$ 265 nm;

MS (ESI, negative mode): m/z 638.07 [M−H]$^-$; 620.07 [M−H+H$_2$O]$^-$ C$_{25}$FH$_{38}$N$_3$O$_{11}$S$_2$ 639.19

BIBLIOGRAPHY

[1] Wester H. J. and Schottelius M. *Ernst. Schering. Res. Found. Workshop* 2007, 79-111.

[2] Lasne M. C., Perrio C, Rouden J., Barre L., Roeda D., Done F., and Crouzel C. *Top. Curr. Chem.* 2002, 222, 201-258.

[3] Welch, M. J., Redvanly, C. S., and Editors. *Handbook of Radiopharmaceuticals: Radiochemistry and Applications* 2003, 848.

[4] Heiss, W.-D. and Hilker, R. *Eur. J. Neurol.* 2004, 11, 5-12.

[5] Ogawa, M., Hatano, K., Oishi, S., Kawasumi, Y., Fujii, N., Kawaguchi, M., Doi, R., Imamura, M., Yamamoto, M., Ajito, K., Mukai, T., Saji, H., and Ito, K. *Nucl. Med. Biol.* 2003, 30, 1-9.

[6] Clark, J. H. *Chem. Rev.* 1980, 80, 429-452.

[7] Harnacher, K., Coenen, H. H., and Stoecklin, G. *J. Nucl. Med.* 1986, 27, 235-238.

[8] Kim H. W., Jeong J. M., Lee Y. S., Chi D. Y., Chung K. H., Lee D. S., Chung J. K., and Lee M. C. *Appl. Radial. Isot.* 2004, 61, 1241-1246.

[9] DuBois, Grant E.; Crosby, Guy A. Dihydrochalcone oligomers. US (1977), U.S. Pat. No. 4,064,167 Ser. No. 19/771, 220

[10] Kim, H.-K. et al., Proton conducting inorganic material, polymer nano-composite membrane including the same, and fuel cell adopting the polymer nano-composite membrane, US 2006/0269816 A1

[11] Deacon, T., Farrar, C. R., Sikkel, B. J., and Williams, A. *J. Am. Chem. Soc.* 1978, 100, 2525-2534.

[12] Roberts D. W. and Williams D. L. *Tetrahedron* 1987, 43, 1027-62.

[13] WO2004113391A2

[14] Cole A. C., Jensen J. L., Ntai I., Tran K. L., Weaver K. J., Forbes D. C., and Davis J. H., Jr. *J. Am. Chem. Soc.* 2002, 124, 5962-5963.

[15] Paetzold, E., Kinting, A., and Oehme, G. *J. Prakt. Chem.* 1987, 329, 725-731.

[16] Suga, K., Miyashige, T., Takada, K., Watanabe, S., and Moriyama, M. *Aust. J. Chem.* 1968, 21, 2333-2339.

[17] Erman, W. and Kretschmar, H. C. *J. Org. Chem.* 1961, 26, 4841-4850.

[18] Zeid, I. and Ismail, I. *Justus Liebigs Annalen der Chemie* 1974, 667-670.

[19] Helberger, J. H., Manecke, G., and Heyden, R. *Justus Liebigs Annalen der Chemie* 1949, 565, 23-35.

[20] King, J. F., Skonieczny, S., and Poole, G. A. *Can. J. Chem.* 1983, 67, 235-243.

[21] Preston A. J., Gallucci J. C., and Paquette L. A. *J. Org. Chem.* 2006, 71, 6573-6578.

[22] King, J. F. and Khemani, K. C. *Can. J. Chem.* 1989, 67, 2162-2172.

LIST OF ABBREVIATIONS

AT Ambient temperature
TFA TrifluoroAcetic Acid
FDG FluoroDeoxyGlucose
AcOF Acetyl hypofluorite (CH$_3$COOF)
OTf Triflate=OSO$_2$CF$_3$
K$_{222}$ 2.2.2. Cryptand
K[$^{18}$F]—F [$^{18}$F] potassium fluoride
K$_2$CO$_3$ Potassium carbonate
H$_2$O Water
CH$_3$CN Acetonitrile
RGD Arginine Glycine Aspartate

The invention claimed is:

1. A method of radiolabelling a macromolecule, comprising:

a. providing a compound of general formula 2

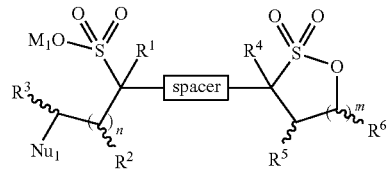

Nu$_1$ = Nucleophile 1
M$_1$ = Counter-ion 1 in which
R$^1$ to R$^6$ groups, identical or different, correspond to hydrogen or an alkyl, an aryl, an arylalkyl, an alkylaryl, an acyl, or a cycloalkyl;
n, m is an integer,
the spacer is a divalent structure;
Nu$_1$ is a nucleophilic radionuclide R*; and,
M$_1$ is a counter-ion;

b. opening the sultone moiety of compound 2 with a nucleophilic macromolecule Ra, thereby yielding a radiolabelled macromolecule of the following general formula 3:

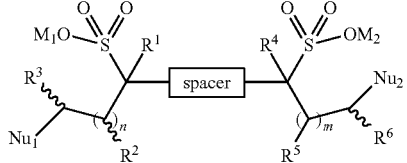

3 wherein
  $Nu_1$ is the radionuclide;
  $Nu_2$ is the macromolecule; and,
  $M_2$ is a counter-ion identical to or different from $M_1$.

2. The method of claim 1, wherein n and m is an integer comprised between 0 and 2.

3. The method of claim 1, wherein $R^3$ to $R^6$ correspond to hydrogen.

4. The method of claim 1, wherein $M_1$ and $M_2$ are monovalent counter-cations.

5. The method of claim 1, wherein said radionuclide is selected from the group consisting of fluorine-18, bromine-76, iodine-123 and iodine-131.

6. The method of claim 1, wherein said macromolecule is selected from the group consisting of: peptide, protein, oligonucleotide, and polynucleotide.

7. A method of radiolabelling a macromolecule, comprising:

a. providing a compound of general formula 2 selected from the group consisting of compound 6a and compound 6b as defined below:

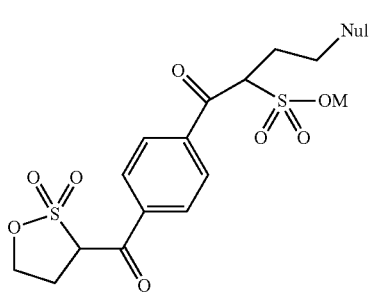

6a

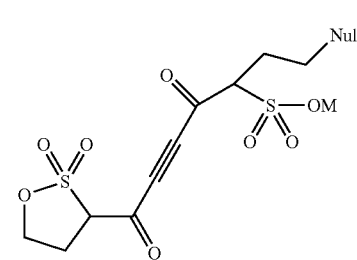

6b wherein $Nu_1$ is a nucleophilic radionuclide R*;
  M is H+ or a counter-ion; and b. opening the sultone moiety of compound 6a or 6b with a nucleophilic macromolecule Ra, thereby yielding a radiolabelled macromolecule.

\* \* \* \* \*